United States Patent [19]

Suetsugi et al.

[11] 3,959,521

[45] May 25, 1976

[54] PROCESS FOR THE FORMATION OF CURED COATINGS

[75] Inventors: Masao Suetsugi, Tokyo; Kozo Sato; Juichi Kobayashi, both of Ohtake; Hideo Nakamoto, Yamaguchi, all of Japan

[73] Assignee: Mitsubishi Rayon Co., Ltd., Tokyo, Japan

[22] Filed: Dec. 6, 1974

[21] Appl. No.: 530,473

Related U.S. Application Data

[63] Continuation-in-part of Ser. No. 319,826, Dec. 29, 1972, abandoned.

[52] U.S. Cl. .................................. 427/44; 427/53; 427/54; 427/407; 427/333; 428/424; 428/425
[51] Int. Cl.² .......................................... B44D 1/50
[58] Field of Search ............... 427/44, 36, 54, 53; 428/424, 425

[56] References Cited
UNITED STATES PATENTS

| | | | |
|---|---|---|---|
| 3,256,133 | 6/1966 | Wright et al. | 428/425 X |
| 3,509,234 | 4/1970 | Burlant et al. | 260/859 |
| 3,560,237 | 2/1971 | Miller | 427/44 |
| 3,652,505 | 3/1972 | Sayigh et al. | 427/44 |
| 3,717,499 | 2/1973 | McClure | 428/425 X |
| 3,749,592 | 7/1973 | Gaske et al. | 427/44 |

*Primary Examiner*—Ralph S. Kendall
*Attorney, Agent, or Firm*—Ladas, Parry, Von Gehr, Goldsmith & Deschamps

[57] ABSTRACT

A process for the formation of an integrated, cured coating which comprises applying to a base material a coating composition containing ethylenically unsaturated groups and free isocyanate groups each in a specific amount to form an undercoat which is subjected to radiation, if desired; further applying a resinous coating composition containing ethylenically unsaturated groups in a specific amount to form a topcoat layer on the undercoat layer; and then curing the topcoat and undercoat layers with radiation to obtain the integrated, cured coating.

5 Claims, No Drawings

PROCESS FOR THE FORMATION OF CURED COATINGS

This is a continuation-in-part of pending application Ser. No. 319,826 filed Dec. 29, 1972, now abandoned.

This invention relates to a process for the formation of a cured coating. More particularly it relates to a process for the formation of an integrated cured coating, which comprises applying to a base material a coating composition (A) containing both ethylenically unsaturated groups and free isocyanate groups, thereafter, if desired, irradiating activating energy rays on an undercoat layer formed on the base material, further applying to the thus-formed undercoat layer a resinous coating composition (B) containing ethylenically unsaturated groups and then irradiating activating energy rays on a topcoat layer formed on the undercoat layer thereby to form on the base material an integrated composite layer exhibiting good corrosion resistance and flexibility in addition to excellent adhesion to the base material.

There has recently been developed a process wherein a resinous composition composed mainly of an unsaturated resin or resins is used as a coating material and such activating energy rays as mentioned above are used as an energy source which will allow a cross-linking reaction to take place in the coating material. This known process is advantageous in that it permits the cross-linking reaction of a coating formed of the coating material to be effected at a relatively low temperature in a short period of time, and therefore, it attracts attention of those concerned with the paint industry as a novel coating technique. Coating materials which may be used for practice of this known process comprise an unsaturated composition composed of at least one member selected from monomers, oligomers, prepolymers and polymers, each containing a polymerizable unsaturated group or groups. When such coating material is coated on a base material to form a filmy coating and then subjected to irradiation by such activating energy rays as mentioned above to effect a cross-linking reaction in the coating, the resulting cross-linked coating will shrink thereby causing such undesired phenomena as warping of the base material, liability to peeling of the coating from the base material and formation of the residual strain in the coating, with the result that various properties of the coating such as adhesion to the base material, impact resistance and flexibility are deteriorated.

The present inventors made researches in the above-mentioned known process for the formation of cross-linked coatings with a view to developing coatings which would overcome the above defects, and they previously proposed a process comprising forming an undercoat layer with a coating material containing free isocyanate groups but being free of unsaturated groups, forming thereon a topcoat layer from a coating material composed mainly of a substance containing polymerizable unsaturated groups, and then subjecting the layer assembly to irradiation by activating energy rays to form an integrated cross-linked coating. According to said proposed process it is possible to obtain a coating excellent in adhesion to the base material and flexibility. Such coating, however, was found still insufficient in adhesion between the undercoat and topcoat layers and in chemical resistance. Therefore, they continued their researches in the proposed process and have now accomplished a process of this invention which can give coatings free of such defects.

The primary object of this invention is to provide a process for the formation of an integrated multi-layer coating which is excellent in corrosion resistance, flexibility, adhesion to a base material on which the coating is formed.

Other objects and advantages of this invention will be apparent from the following description.

These objects are accomplished by the practice of a process which comprises applying to a base material a coating composition (A) containing both ethylenically unsaturated group or groups and free isocyanate group or groups, thereby to form an undercoat layer on the base material, irradiating activating energy rays upon the thus-formed undercoat, further applying to the irradiated undercoat a resinous coating composition (B) in which ethylenically unsaturated group or groups are present to form a topcoat layer thereon, and then irradiating activating energy rays upon the topcoat layer thereby to obtain an integrated two-layer coating on the base material. Repetition of this procedure will make it possible to form an integrated multi-layer (two- or more-layer) coating.

The coating composition (A) consists essentially of one member selected from the group consisting of (a) an unsaturated isocyanate compound containing both as many ethylenically unsaturated groups as calculated from the formula $$0.5 \text{ to } 12 \times \frac{\text{Molecular Weight of Unsaturated Isocyanate Compound}}{1000}$$

and free isocyanate groups in an amount of 0.5 to 30% by weight of the coating composition (A), (b) a mixture of an unsaturated compound containing as many ethylenically unsaturated groups as calculated from the formula $$0.5 \text{ to } 12 \times \frac{\text{Molecular Weight of Unsaturated Compound}}{1000}$$

and a saturated or unsaturated isocyanate compound containing free isocyanate groups in an amount of 0.5 to 30% by weight of the coating composition (A), and (c) a mixture of the material (a) or (b) and a resinous saturated compound.

The resinous coating composition (B) consists essentially of a material such as (d) an unsaturated polyester, (e) a mixture of an acrylic polymer containing at least one hydroxyl, glycidyl, isocyanate or carboxylic group and a vinyl monomer containing at least one group that is reactive with any one of these groups, (f) a dimethacryloyl-terminated polyester, (g) a methacrylatemodified epoxy resin or the like, the materials (d), (e), (f) and (g) each containing 0.5 to 12 ethylenically unsaturated groups (or bonds) per 1000 of the molecular weight of the unsaturated material in the resinous coating composition (B).

By the terms "an unsaturated compound having 0.5 to 12 ethylenically unsaturated groups per 1000 of the molecular weight thereof" is meant an unsaturated compound containing as many curable unsaturated groups as calculated from the formula $$0.5 \text{ to } 12 \times \frac{\text{Molecular Weight of Compound}}{1000}$$

This will also be understood by illustrating that if an unsaturated compound has 3 ethylenically unsaturated groups and a molecular weight of 6000, it follows that the compound has 0.5 (3/6) ethylenically unsaturated groups per 1000 of the molecular weight thereof.

The dosage necessary to give to the undercoat layer and topcoat layer for their curing ranges form 1 to 20 Mrad, and it is obtained either by supplying the dosage at a dose rate of from 1 – 20 Mrad/sec by the use of an electron beam accelerator at an acceleration voltage of from 150 to 750 Kev or by supplying the dosage by the use of a mercury lamp irradiating at an output of from 80 to 200 watt/inch for 5 – 30 seconds in the air or for 1 – 30 seconds in an inert atmosphere filled with nitrogen for example.

If the free isocyanate group content is less than 0.5% by weight, the resulting cross-linked coating will be insufficient in adhesion to the base material and in adhesion between the undercoat and topcoat layers, and since it is impossible to release sufficiently the strain formed in the coating by the shrinkage thereof during the cross-linking reaction under the influence of the activating energy rays, it is difficult to obtain a coating excellent in physical properties such as flexibility and impact resistance. On the other hand, if a coating composition having a free isocyanate group content exceeding 30% by weight is used for forming an undercoat layer on a base material, the weatherability, water resistance and chemical resistance of the resulting cross-linked coating will be poor, though it is possible to improve the coating in adhesion to the base material and adhesion between the undercoat and topcoat layers and to release sufficiently the strain formed during the cross-linking reaction. Further, the coating composition comprising free isocyanate groups in such too great an amount is readily affected by moisture in the air and hence, it is difficult to maintain the properties of the coating composition always at constant levels. Therefore, it will be very difficult to obtain a coating having invariably satisfactory properties from the coating material. Still further, since the free isocyanate groups having a high reactivity tend to remain in the undercoat layer of the resulting cross-linked coating formed of the coating material having such too high a free isocyanate group content as exceeds 30% by weight, the resulting cross-linked coating tends to change in properties with the lapse of time.

For these reasons, in this invention it is specified that the free isocyanate group content of the coating material (A) is 0.5 to 30% by weight, preferably 1 to 10% by weight.

Saturated or unsaturated isocyanate compounds containing at least one free isocyanate group are used as the isocyanate group source in the coating material (A). The saturated isocyanate compounds used herein include aliphatic and aromatic diisocyanates expressed by the following general formula (I)

OCN—R—NCO     (I)

wherein R stands for an aliphatic group such as ethylene, propylene, hexylene, thiodiethylene, hexamethylene, 3-methoxyhexylene and ω, ω '-dipropyl ether groups, a divalent aromatic group such as substituted and unsubstituted phenylene and naphthalene groups.

Examples of such aromatic diisocyanates include tolylene diisocyanate, xylylene diisocyanate, diphenylmethane diisocyanate, m-phenylene diisocyanate, naphthalene diisocyanate and biphenylene diisocyanate. Examples of such aliphatic diisocyanate are ethylene, propylene, hexylene, thiodiethylene, hexamethylene, 3-methoxyhexylene and ω, ω '-dipropylether diisocyanates.

The saturated isocyanate compounds used herein further include addition reaction products prepared from such aliphatic or aromatic diisocyanates as mentioned above and compounds containing an active hydrogen atom such as water and polyols, e.g., ethylene glycol, propylene glycol, diethylene glycol, trimethylol propane and glycerin as well as polymers having an active hydrogen atom, such as saponified products of vinyl acetate homopolymers and copolymers, homopolymers of hydroxyl group-containing vinyl monomers obtained by esterification between α,β-monoethylenically unsaturated carboxylic acids such as acrylic acid, methacrylic acid, maleic acid and itaconic acid, and polyols such as ethylene glycol, propylene glycol and tetraethylene glycol, and copolymers of hydroxyl group-containing vinyl monomers with comonomers such as methyl methacrylate, methyl acrylate, ethyl acrylate, ethyl methacrylate, propyl acrylate, propyl methacrylate, butyl acrylate, butyl methacrylate, hexyl acrylate, hexyl methacrylate, 2-ethylhexyl acrylate, 2-ethylhexyl methacrylate, lauryl acrylate, lauryl methacrylate, benzyl acrylate, benzyl methacrylate, styrene, acrylonitrile, methacrylonitrile and vinyl chloride.

The unsaturated isocyanate compounds having in the molecule at least one free isocyanate group and at least one polymerizable unsaturated group can be prepared by the reactions expressed by the following formulae:

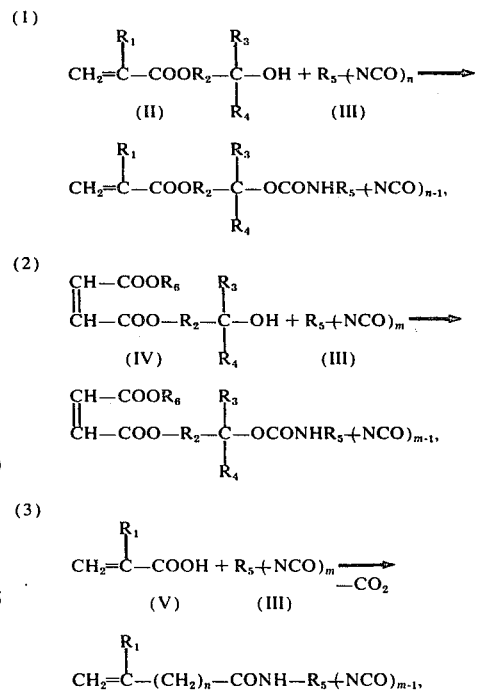

(4)

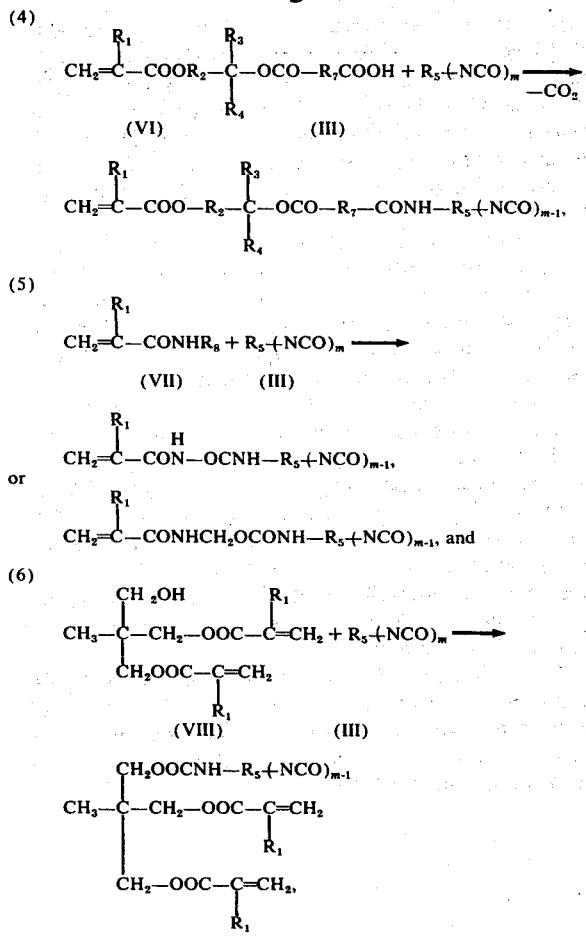

(5)

(6)

wherein $R_1$ stands for a hydrogen atom, a methyl group or a group —$COOR_9$ in which $R_9$ is an alkyl group having 1 to 18 carbon atoms; $R_2$ stands for a group

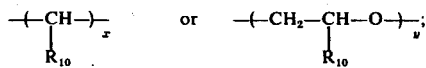

$R_3$ and $R_4$ stand for a hydrogen atom or an alkyl group having 1 to 5 carbon atoms; $R_5$ is a divalent aromatic or aliphatic hydrocarbon radical; $R_6$ stands for an alkyl group having 1 to 18 carbon atoms; $R_7$ stands for a group —$CH_2CH_2$— or —CH=CH— or an orthophenylene group; $R_8$ is a hydrogen atom or a methylol group; $R_{10}$ designates an alkyl group having 1 to 4 carbon atoms; $m$ is an integer of at least 2; $n$ is an integer of from 0 to 2; and $x$ and $y$ are integers of from 1 to 10.

The compounds of the formula (II) or (IV) to be used as the starting material for obtaining the aforesaid unsaturated isocyanate compounds, include monoester compounds obtained by reacting a monoester of an $\alpha,\beta$-monoethylenically unsaturated mono- or dicarboxylic acid such as a monoester of acrylic, methacrylic, itaconic or maleic acid and a monoester of $\alpha$-methyleneglutaric acid, with a polyol such as ethylene glycol, propylene glycol or hexylene glycol.

The compounds of the formula (III) include aliphatic and aromatic polyisocyanates containing at least two free isocyanate groups, such as those expressed by the above formula (I).

The compounds of the general formula (V) include, for example, acrylic acid and methacrylic acid.

The compounds of the general formula (VI) include compounds obtained by reacting hydroxyl group-containing vinyl monomers expressed by the above formula (II) with carboxylic anhydrides such as malonic anhydride, itaconic anhydride, himic anhydride (1, 4, 5, 6, 7, 7-hexachloro-bicyclo-[2, 2, 1]-hepta-6-en-2, 3-dicarboxylic acid anhydride), succinic anhydride, maleic anhydride, phthalic anhydride and tetrahydrophthalic anhydride.

Examples of the compounds expressed by the general formula (VII) are acrylamide, methacrylamide, methylol acrylamide and methylol methacrylamide.

Diesters obtained by reacting trimethylol propane with an $\alpha,\beta$-monoethylenically unsaturated monocarboxylic acid such as acrylic acid or methacrylic acid are among the compounds of the formula (VIII).

In this invention, it is essential that the unsaturated compound or compounds which may be used in the preparation of the coating composition (A) should have 0.5 to 12 olefinic unsaturated groups (or bonds) per 1000 of the molecular weight. If a coating composition which is the same as the composition (A) except its olefinic unsaturated group content of less than 0.5 per 1000 of the molecular weight is used, it will exhibit a low cross-linking reactivity under irradiation energy rays, and it is therefore difficult to obtain therefrom a cross-linked coating having excellent properties. On the other hand, if there is used a coating composition having more than 12 ethylenically unsaturated groups per 1000 of the molecular weight, the density of cross-linking attained under irradiation of activating energy rays will be too high, and it is, therefore, difficult to obtain a coating excellent in adhesion to a base material, impact resistance, flexibility and adhesion between the undercoat and topcoat layers when the composition is applied to the base material.

Examples of the unsaturated compounds having such characteristics according to this invention are as follows:

C. Unsaturated polyesters obtained by condensing an unsaturated polycarboxylic acid selected from maleic acid and itaconic acid,

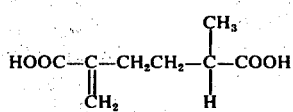

or a combination of such unsaturated polycarboxylic acid and a non-polymerizable polycarboxylic acid such as succinic acid, adipic acid, sebacic acid, tetrahydrophthalic acid or terephthalic acid, with a polyhydric alcohol.

D. (D-1). Unsaturated polyesters or unsaturated vinyl polymers having the recurring units expressed by the following formula (XI):

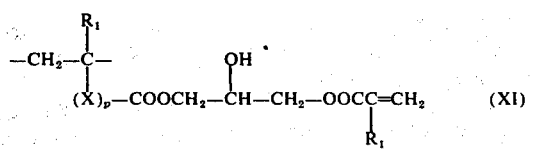

wherein $R_1$ is as defined above, X is —$CH_2OOCR_7$— or

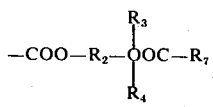

in which $R_2$, $R_3$ and $R_4$ are as defined above and $R_7$ is —CH$_2$CH$_2$—, —CH=CH—, o-phenylene,

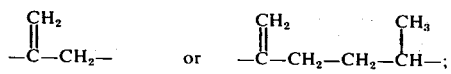

and $p$ is an integer of 0 or 1, which polyesters or vinyl polymers are prepared by addition reaction between polyesters or vinyl polymers having the recurring units expressed by the following formula (IX):

wherein $R_1$, X and $p$ are as defined above, and glycidyl esters of unsaturated carboxylic acids expressed by the following formula (X):

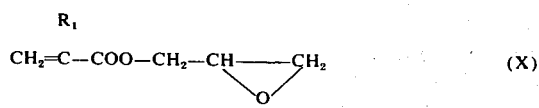

wherein $R_1$ is as defined above.

The unsaturated polyesters having the recurring units expressed by the formula (XI) can be prepared by the following procedures:

At first, a polyhydric alcohol having at least three hydroxyl groups such as trimethylol propane or glycerine or a combination of such polyhydric alcohol with a dihydric alcohol such as ethylene glycol, propylene glycol, diethylene glycol or bis-phenol A is polycondensed with at least one polycarboxylic acid selected from succinic acid, maleic acid, adipic acid, phthalic acid, terephthalic acid, isophthaoic acid, itaconic acid and $\alpha$-methyleneglutaric acid, to thereby obtain a hydroxyl group-containing polyester. Then, the resulting hydroxyl group-containing polyester is reacted with such a polybasic acid anhydride as succinic anhydride, maleic anhydride, phthalic anhydride, itaconic anhydride and $\alpha$-methyleneglutaric anhydride, to thereby form a polyester having carboxylic acid groups. The so-formed polyester is subjected to addition reaction with a glycidyl ester of an unsaturated carboxylic acid expressed by the formula (X), whereby an unsaturated polyester having the recurring units expressed by the formuls (XI) is obtained.

The unsaturated vinyl polymers having the recurring units expressed by the formula (XI) can be prepared by the following methods:

i. At first, a vinyl polymer having the recurring units expressed by the formula (IX) is prepared by copolymerizing an $\alpha,\beta$-olefinically unsaturated carboxylic acid such as acrylic acid or methacrylic acid with other vinyl monomer such as methyl methacrylate, ethyl acrylate, butyl acrylate, butyl methacrylate, 2-ethylhexyl acrylate, 2-ethylhexyl methacrylate, styrene, acrylonitrile, methacrylonitrile or vinyl chloride, and the resulting vinyl polymer is reacted with an unsaturated carboxylic acid glycidyl ester expressed by the formula (X).

ii. At first, an $\alpha,\beta$-ethylenically unsaturated carboxylic acid hydroxyalkyl ester expressed by the aforementioned general formula (II) is copolymerized with other vinyl monomer such as exemplified in (i) above, to thereby form a hydroxyl group-containing vinyl polymer. Then, this hydroxy group-containing vinyl polymer is reacted with a carboxylic acid anhydride such as succinic anhydride, maleic anhydride, phthalic anhydride or itaconic anhydride, to thereby form a vinyl polymer having the recurring units expressed by the formula (IX). Then, this carboxylic acid-containing vinyl polymer is subjected to addition reaction with an unsaturated carboxylic acid glycidyl ester expressed by the above formula (X), whereby an unsaturated vinyl polymer having the recurring units expressed by the formula (XI) is obtained.

(D-2). Unsaturated vinyl polymers having the recurring units expressed by the formula (XI), which polymers are prepared by addition reaction between a vinyl polymer having the recurring units expressed by the following formula (XII):

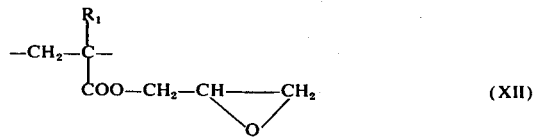

wherein $R_1$ is as defined above, and an $\alpha,\beta$-ethylenically unsaturated carboxylic acid expressed by the following formula (XIII):

wherein $R_1$ is as defined above.

These unsaturated vinyl polymers expressed by the formula (XI) can be prepared by the following procedures:

At first, a vinyl polymer having the recurring units expressed by the formula (XII) is prepared by copolymerizing a glycidyl ester of an $\alpha,\beta$-ethylenically unsaturated carboxylic acid such as acrylic acid or methacrylic acid with other vinyl monomer such as exemplified in (D-1), (i) above, and this glycidyl ester group-containing vinyl polymer is reacted with an $\alpha,\beta$-ethylenically unsaturated carboxylic acid expressed by the formula (XII), such as acrylic acid or methacrylic acid, whereby an unsaturated vinyl polymer having the recurring units expressed by the formula (XI) can be obtained.

(D-3). Vinyl polymers having the recurring units expressed by the following formula (XVI):

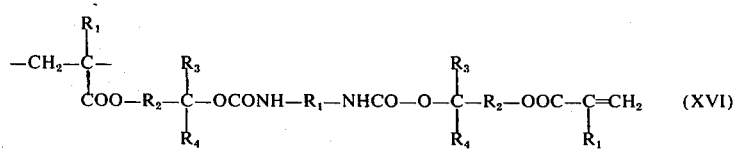

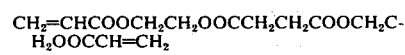

wherein $R_1$, $R_2$, $R_3$, $R_4$ and $R_5$ are as defined above, which vinyl polymers are prepared by subjecting a hydroxyl group-containing polymer expressed by the following formula (XIV):

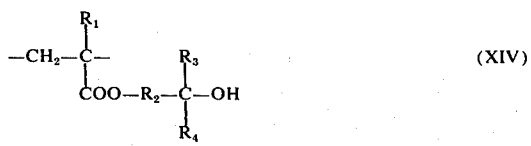

wherein $R_1$, $R_2$, $R_3$ and $R_4$ are as defined above, to addition reaction with a polyisocyanate expressed by the aforementioned formula (I), to thereby form a free isocyanate group-containing vinyl polymer having the recurring units expressed by the following formula (XV):

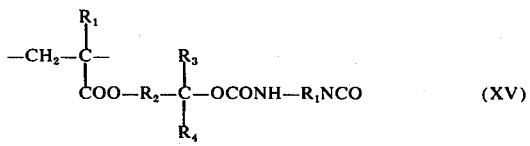

wherein $R_1$, $R_2$, $R_3$ and $R_4$ are as defined above, and reacting at least a part of the free isocyanate groups contained in the resulting vinyl polymer (XV) with a hydroxyalkyl ester of acrylic acid or methacrylic acid. (D-3). Di(meth)acryloyl-terminated polyesters of the following formula (XVIII):

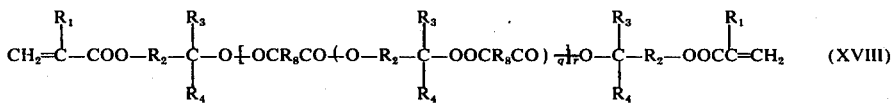

wherein $R_1$, $R_2$, $R_3$ and $R_4$ are as defined above, $R_8$ is a hydrocarbon residue having 2 to 10 carbon atoms, $q$ is an integer of from 0 to 14 and $r$ is an integer of from 1 to 14,
which polyesters are formed by reacting a linear, hydroxylterminated, low-molecular weight polyester expressed by the following formula (XVII):

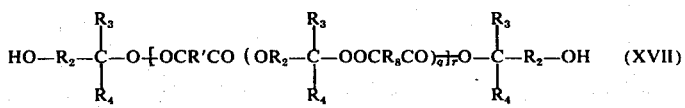

wherein $R_2$, $R_3$, $R_4$, $q$ and $r$ are as defined above, and $R'$ is a divalent aromatic or aliphatic radical, with at least one member selected from acrylic acid, methacrylic acid and halides of these acids.

These hydroxy group-containing polyesters can be prepared, for example, by the following method.

Succinic acid and ethylene glycol are subjected to dehydration condensation at a molar rator of 2 : 1 to obtain a hydroxyl group-containing polyester expressed by the following formula

HOCH$_2$CH$_2$OOCCH$_2$CH$_2$COOCH$_2$CH$_2$OH and this polyester is subjected to dehydration condensation reaction with acrylic acid to obtain a diacryloyl-terminated polyester of the following formula

CH$_2$=CHCOOCH$_2$CH$_2$OOCCH$_2$CH$_2$COOCH$_2$CH$_2$OOCCH=CH$_2$ (D-5). (Meth)acryloyl-terminated epoxy compounds prepared by subjecting at least one member selected from α,β-ethylenically unsaturated carboxylic acids such as acrylic acid and methacrylic acid to addition reaction with a polyepoxy compound having an epoxy equivalent of from 100 to 1000 and a molecular weight of from 100 to 1500.

The polyepoxy compounds which may be used for formation of such (meth)acryloyl-terminated epoxy compounds, include products obtained by reaction between bis-phenol A and epichlorohydrin.

(D-6). Other unsaturated compounds which may be used include esters obtained by reacting acrylic acid or methacrylic acid with a monohydric alcohol such as methanol, ethanol, propanol, isopropanol, butanol, hexanol, 2-ethylhexanol, cyclohexanol or lauryl alcohol, and further include vinyl acetate, vinyl propionate, vinyl chloride, vinylidene chloride, styrene, α-methylstyrene, chlorostyrene, acrylamide, methacrylamide, methylene-bis-acrylamide and trimethylol propane triacrylate.

As mentioned above, the resinous coating composition (B) for forming a topcoat layer comprises an unsaturated compound containing 0.5 to 12 ethylenically unsaturated groups per 1000 of the molecular weight thereof. This unsaturated compound of the coating composition (B) is appropriately selected from compounds (C), (D-1) to (D-6) illustrated above with respect to the unsaturated compound or compounds in the coating composition (A).

If there is used a comparative resinous coating composition which is the same as the composition (B) except that its unsaturated group content is less than 0.5 per 1000 of the molecular weight thereof, a sufficient degree of cross-linking will be unable to be attained in a topcoat layer formed of the comparative composition under the irradiation of activating energy rays, thereby making it difficult to obtain a cross-linked coating excellent in such properties as hardness, water resistance, solvent resistance, weatherproofing and corrosion resistance. On the other hand, if there is used under the irradiation of activating energy rays another comparative composition which is the same as the composition (B) except that its unsaturated group content exceeds 12 per 1000 of the molecular weight thereof, it will readily be cross-linked to form a cured coating which has an excessively high degree of cross-linking and a drastically lowered flexibility and impact resistance, thereby making it impossible to obtain a desired cured coating having excellent properties.

The coating composition (A) may be incorporated with a phosphate, a chromate such as strontium chromate or zinc chromate, or the like if necessary.

In the practice of the process of this invention, a coating composition (A) is applied to a base material to form an undercoat layer thereon, a resinous coating composition (B) is applied to the thus-formed undercoat layer to thereby form a topcoat layer, and then the layer assembly is subjected to irradiation of activating energy rays such as electron beam or light having a wave length of 2000 – 8000 A, whereby a desired, cured and cross-linked coating can be obtained.

It is possible to form a topcoat layer of the coating composition (B) on an undercoat layer of the coating composition (A) without cross-linking of the undercoat layer, but especially good results are obtained by the formation of the topcoat layer on the undercoat layer after the latter has been partially cross-linked by allowing it to stand still or heating it to 50°– 300°C., or by exposing it to irradiation of activating energy rays such as electron beam and light having a wavelength of from 2000 to 8000 A.

As the coating composition (A), there may be used a mixture of a saturated thermoplastic polymer which is a homopolymer or copolymer of (meth)acrylic monomer expressed by the following formula (XX)

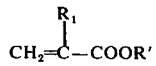

wherein $R_1$ is defined above and $R'$ is an alkyl group having 1 to 18 carbon atoms, and the unsaturated compounds and isocyanate group-containing compounds expressed at the aforesaid (C) and (D-1) to (D-6).

The alkyl group $R'$ of the above alkyl acrylate or methacrylate includes methyl, ethyl, propyl, butyl, 2-ethylhexyl, lauryl, cyclohexyl or stearyl group. In addition, polyvinyl chloride and a copolymer of vinyl chloride with vinyl acetate can be used as the above-mentioned saturated thermoplastic polymer. Still further, the foregoing saturated thermoplastic polymers may be copolymerized up to 10% by weight, based on the total saturated thermoplastic polymer, of other copolymerizable vinyl monomer free of an active hydrogen atom, such as styrene, acrylonitrile, acrylamide, methacrylamide, dialkylaminoethyl acrylate or dialkylaminoethyl methacrylate. It is essential that such thermoplastic polymer should have a molecular weight of from 10,000 to 300,000. If a saturated thermoplastic polymer having a molecular weight not exceeding 10,000 is used in an attempt for the formation of a coating of the composition (A), the resulting cross-linked coating will be insufficient in both physical and chemical properties. If the saturated thermoplastic polymer having a molecular weight exceeding 300,000 is used, it will not exhibit a sufficient solubility in the isocyanate group-containing compound to be used for the formation of a coating of the composition (A), thereby rendering it difficult to form a coating composition such as the one (A) whose coating will have satisfactory properties substantially invariable against the lapse of time.

Unlike conventional isocyanate type paints, the coating composition (A) containing the saturated thermoplastic polymer having the abovementioned characteristics is hardly affected by moisture in the air, and it is therefore quite easy to handle. Further, such coating material (A) is advantageous in that it exhibits an excellent moldability at the time of formation of a coating thereof, and a coating obtained by cross-linking the coating composition (A) is quite excellent in flexibility.

It is desired that this thermoplastic polymer is contained in the coating composition (A) at a concentration of from 5 to 50% by weight. At a concentration below 5% by weight, the effects of this invention such as mentioned above cannot be attained in such low concentrated composition, and at a concentration exceeding 50% by weight, such high concentrated coating composition will give a coating having lowered workability and physical and chemical properties.

Since the coating composition (A) comprises as the functional elements the specified amounts of ethylenically unsaturated groups and free isocyanate groups and the resinous coating composition (B) comprises as the functional elements the specified amounts of ethylenically unsaturated groups, there can be attained a very good adhesion between the undercoat layer formed of the coating composition (A) and the topcoat layer formed of the coating composition (B), thereby making it possible to obtain a cross-linked composite coating having excellent properties.

In accordance with one of preferred embodiments of the process of this invention, after the undercoat layer has been formed on the base material, it is subjected to irradiation of rays having a wavelength of 2000 to 8000 A or electron beam in an atmosphere having an oxygen content of at least 0.2%, especially at least 1%, to thereby partially cross-link and cure the undercoat layer, the coating composition (B) is coated on the undercoat layer to form a topcoat layer thereon, and then the layer assembly is subjected to irradiation of rays having a wavelength of 2000 to 8000 A or electron beam to thereby form a cured, cross-linked coating. In this embodiment, the resulting cured, cross-linked coating is quite excellent in not only adhesion to the base material and adhesion between the topcoat layer and undercoat layer but also properties such as flexibility and chemical resistance.

In the presence of this invention, the coating composition (A) comprising as the functional elements free isocyanate groups and ethylenically unsaturated groups is used for the formation of an undercoat layer and the coating composition (B) comprising as the functional element ethylenic unsaturation is used for the formation of a topcoat layer, and the resulting composite layer is subjected to the irradiation of light or electron beam to cure and cross-link the composite layer. By dint of this specific combination of the coating compositions for the formation of the undercoat and topcoat layers under the influence of irradiaton of activating energy rays as the cross-linking means, the resulting coating can exhibit excellent adhesion to the base material and excellent adhesion between the undercoat and topcoat layers and can possess good impact strength with less internal strain caused by the shrinkage thereof at the cross-linking step, as well as good chemical resistance, good water resistance and other excellent characteristics.

The curing and cross-linking of the composite layer structure composed of the undercoat layer and topcoat layer can be accomplished by subjecting it to the irradiation of activating energy rays such as light having a wavelength of 2000 to 8000 A or radiant rays, e.g., electron beam. In case light is used as the activating energy rays, it is desirable that either of the coating compositions (A) and (B) should be incorporated with 0.1 to 5% by weight of a photopolymerization initiator such as carbonyl compounds, e.g., benzoin, benzoin methyl ether, benzoin isobutyl ether, benzoin isopropyl ether, benzyl and butyroin; and polynuclear quinones, e.g., anthraquinone, chloroanthraquinone and t-butylanthraquinone.

In case radiant rays are used as the activating energy rays, best results are obtained by employing an electron accelerator having an accelerating voltage of 0.1 to 2 Kev thereby to apply electron beam at a dose rate of 0.1 to 20 Mrad/sec under such conditions that the absorbed dose of 0.1 to 20 Mrad can be attained, as previously mentioned. Further, in case radiant rays are employed as the activating energy rays, it is not always necessary to cure the undercoat layer in advance, and it is sufficient to conduct irradiation of radiant rays only once on a topcoat layer after the formation thereof, whereby the intended coating can be obtained.

The defects of conventional coatings obtained by the irradiation of radiant rays, namely inferior adhesion to the base material and poor impact resistance, can be highly reduced by the process of this invention. Such excellent effects of this invention are made especially prominent when metallic materials which are originally capable of extremely low adhesion to conventional coatings are used as the base material in the practice of the present invention. In order to improve the adhesion of the conventional coatings to the metallic materials such as steel plates and aluminum plates and also improve processability of coatings formed on such metallic materials, it has heretofore been conducted to subject such metallic materials to chemical treatments with, for example, a phosphate, chromite or the like. When the coating compositions of this invention are applied to a metallic base material previously subjected to such chemical treatment and the assembly was exposed to the irradiation of activating energy rays, the resulting cured coating will exhibit excellent adhesion to the base material, excellent impact resistance and excellent after processability, without troubles encountered due to the residual strain caused by shrinkage of the coating at the curing step. When a non-metallic base is used in the practice of this invention, it is not necessary to subject the base to surface treatment before coated.

In short, in accordance with this invention, it is possible to form on a metallic base material a coating which has excellent after processability and good corrosion resistance. The reason for this is as follows. According to this invention, the integrated, cured coating is obtained, for example, by coating to a thickness of 0.01 – 10 $\mu$ on a base material a primer (coating composition (A)) comprising an unsaturated compound containing isocyanate groups in an amount of 0.5 – 30% by weight of the primer and also containing as many curable ethylenically unsaturated groups as calculated from the formula $$0.5 \text{ to } 12 \times \frac{\text{Molecular Weight of Unsaturated Compound}}{1000}$$

to form on the base material an undercoat layer, subjecting the undercoat layer to the irradiation of the activating energy rays if desired, further coating to a thickness of 5 – 100 $\mu$ on the undercoat layer a topcoat paint (resinous coating composition (B)) comprising an unsaturated compound containing as many curable ethylenically unsaturated groups as calculated from the formula $$0.5 \text{ to } 12 \times \frac{\text{Molecular Weight of Unsaturated Compound}}{1000}$$

to form a topcoat layer on the undercoat layer, and then subjecting the topcoat and undercoat layers to the irradiation of the activating energy rays thereby obtaining the integrated, cured coating. In this case, the presence of the isocyanate groups in the primer not only greatly reduces the inner strain of the undercoat layer due to the shrinkage thereof which would be caused when the layer is cured, but also permits the layer to adhere excellently tightly to the base material. In addition, the presence of the polymerizable, ethylenically unsaturated groups in the primer permits a chemical bond or combination between the undercoat and topcoat layers when the topcoat layer is cured, thereby further strengthening the adhesion of the integrated coating to the base material in combination with said effect obtained by the presence of the isocyanate groups in the primer.

This invention will now be illustrated by reference to examples.

Preparation of Unsaturated Compound Having 0.5 to 12 Ethylenically Unsaturated Groups Per 1000 of Molecular Weight THEREOF 1. A condensation vessel was charged with 49 parts of maleic anhydride, 36.5 parts of adipic acid, 37 parts of phthalic anhydride and 83.6 parts of propylene glycol to form a mixture thereof which was subjected to dehydrating condensation at 185°C in a nitrogen atmosphere. The dehydrating condensation was continued for 10 hours while distilling off water produced during the condensation to remove the water from the reaction system in order to obtain an unsaturated polyester having a molecular weight of about 1300. An unsaturated resin solution (1) was formed by mixing 70 parts of the unsaturated polyester so obtained and 30 parts of styrene.

2. The same reaction vessel as used in said (1) was charged with 130 parts of 2-hydroxyethyl methacrylate, 100 parts of succinic anhydride and 0.3 part of hydroquinone monomethyl ether. The materials so charged were reacted at 130°C for 20 minutes and then incorporated with 31 parts of ethylene glycol, 400 parts of toluene and 3 parts of p-toluene sulfonic acid, and the resulting mixture was subjected to dehydration condensation reaction at the reflux temperature for 4 hours. The resulting reaction mixture so condensed was neutralized by addition of sodium bicarbonate and filtered. Removal of the toluene gave a liquid unsaturated polyester represented by the following structural formula

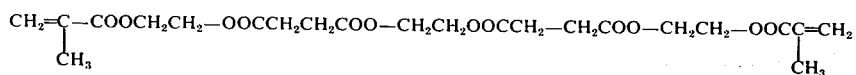

The resulting liquid unsaturated polyester resin was designated as an unsaturated resin solution (2).

3. A reaction vessel was charged with 75 parts of adipic acid, 124 parts of glycidyl acrylate, 5 parts of dimethylaminoethyl methacrylate and 0.1 part of hydroquinone monomethyl ether, and the inside atmosphere of the reaction vessel was purged with nitrogen. They were reacted at 90°C. for 6 hours to obtain an unsaturated resin solution (3) comprising an unsaturated compound having the following structural formula

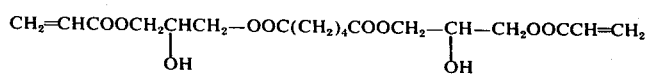

and dimethylaminoethyl methacrylate.

4. A reaction vessel was charged with 12 parts of ethylene diamine, 39 parts of maleic anhydride and 100 parts of toluene, and they were reacted at 100°C. for 1 hour to produce a reaction mixture. Then, 51.2 parts of glycidyl acrylate, 0.3 parts of hydroquinone monomethyl ether and 3 parts of dimethylaminoethyl methacrylate were added to the reaction mixture. The reaction was further carried out for 4 hours to obtain an unsaturated resin solution (4) composed mainly of an unsaturated compound having the following structural formula

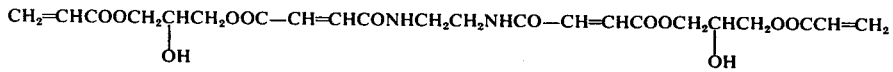

and dimethylaminoethyl methacrylate.

5. A cell was charged with a mixture of 20 parts of methyl methacrylate, 30 parts of butyl acrylate, 20 parts of styrene, 30 parts of 2-hydroxyethyl methacrylate, 3 parts of t-dodecyl mercaptan and 2 parts of benzoyl peroxide, and the mixture was subjected to cast-polymerization at 98°C. for 5 hours to obtain a hydroxyl group-containing polymer having a molecular weight of about 9000. Then, 100 parts of the polymer so formed was dissolved in a solution consisting of 100 parts of benzyl acrylate, 100 parts of 2-ethylhexyl acrylate and 0.1 part of hydroquinone monomethyl ether, following which 30 parts of phthalic anhydride and 2 parts of dimethylaminoethyl methacrylate were added to the resulting solution and the reaction was carried out at 90°C. for 2 hours. Then, 35 parts of glycidyl acrylate was added to the reaction mixture and the reaction was further conducted at 90°C. for 5 hours to obtain an unsaturated resin solution (5) containing an unsaturated compound having the recurring units expressed by the following formula

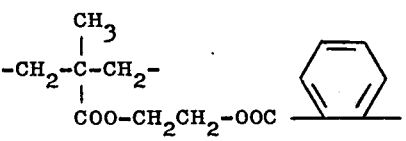

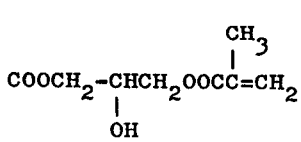

6. A reaction vessel was charged with a mixture of 134 parts of trimethylol propane, 144 parts of acrylic acid, 100 parts of toluene and 3 parts of p-toluenesulfonic acid, and the dehydration condensation reaction was carried out for 6 hours at the reflux temperature of the mixture. The resulting reaction solution was neutralized by addition of sodium bicarbonate, and the precipitated sodium p-toluene sulfonate was separated by filtration. Distillation of the toluene gave a solution (6) comprising an unsaturated compound having the following structural formula

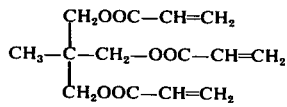

Preparation of Free Isocyanate Group-Containing Compounds

I. A reaction vessel was charged with a solution of 43 parts of the hydroxyl group-containing unsaturated compound obtained in said (3) in 50 parts of toluene and 0.1 part of hydroquinone. The solution so charged was raised in temperature to 50°C. and then incorporated dropwise with 50 parts of 2,4-tolylene diisocyanate over a period of 5 hours to effect the reaction. Distillation of the toluene from the resulting liquid reaction mixture gave a free isocyanate group-containing compound (I) having the following structural formula

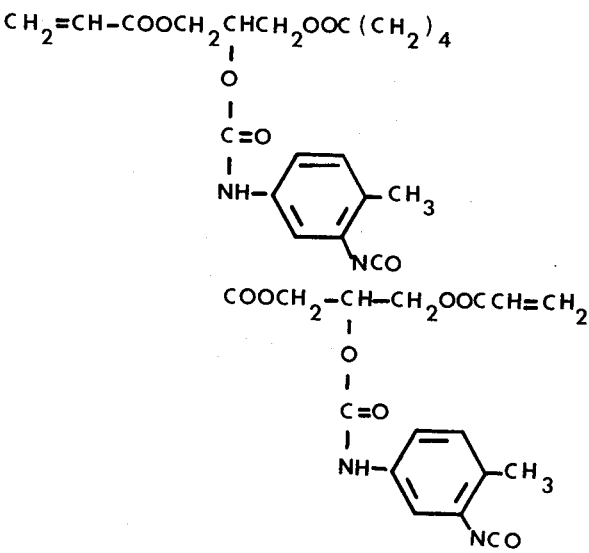

II. A reaction vessel was charged with 116 parts of 2-hydroxyethyl acrylate, 100 parts of succinic anhydride, 5 parts of dimethylaminoethyl methacrylate and 0.2 part of hydroquinone monomethyl ether, and the inside atmosphere of the reaction vessel was replaced by nitrogen. Then, the reaction was carried out at 90°C. for 20 minutes. To the resulting reaction solution were added 100 parts of toluene and 159 parts of 2,4-tolylene diisocyanate, and the reaction was conducted at 50°C. for 5 hours to obtain a free isocyanate group-containing compound (II) having the following structural formula

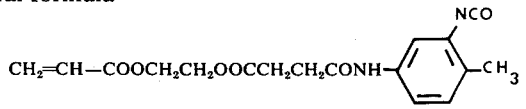

III. A reaction vessel was charged with 126 parts of hexamethylene diisocyanate, 300 parts of ethyl acetate and 5 parts of tributyl amine to form a solution thereof which was raised in temperature to 50°C. Then, 188 parts of methyl-2-hydroxyethyl itaconate was added dropwise to the solution at 50°C. over a period of time of 5 hours, and the reaction was continued for another 3 hours to obtain a free isocyanate group-containing compound (III) having the following structural formula

IV. A reaction vessel was charged with 160 parts of 1,3-phenylene diisocyanate, 200 parts of ethyl acetate and 5 parts of 2-vinylpyridine to form a solution thereof, and the temperature of the solution was elevated to 80°C., after which 85 parts of methacrylamide was added dropwise to the solution over a period of 5 hours to effect the reaction. A free isocyanate group-containing compound (IV) having the following structural formula

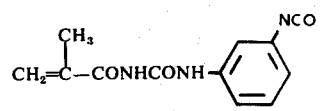

was thus obtained.

V. A reaction vessel was charged with 188 parts of xylidene diisocyanate, 5 parts of dimethylaminoethyl methacrylate and 300 parts of toluene, and the temperature of the charge was raised to 50°C., following which 130 parts of 2-hydroxyethyl methacrylate was added dropwise to the charge over a period of 7 hours to effect the reaction and obtain a free isocyanate group-containing compound (V) having the following structural formula

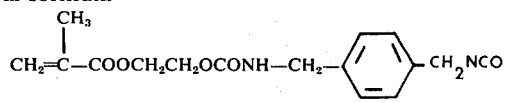

VI. A reaction vessel was charged with 116 parts of maleic acid, 318 parts of 2,4-tolylene diisocyanate and toluene, and they were reacted at 70°C, for 5 hours to obtain a free isocyanate group-containing compound (VI) having the following structural formula

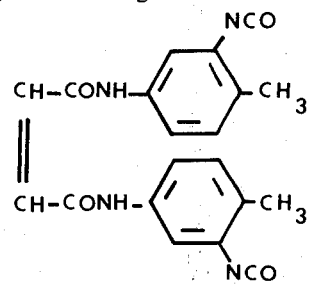

EXAMPLE 1

A coating composition (A) indicated in Table 1 was coated to a thickness of 5μ on a phosphatized steel plate previously subjected to a zinc phosphate treatment (grade = JIS 3302; thickness = 0.278 mm) to thereby form an undercoat layer, and the coated plate was treated under conditions indicated in Table 1. Thus there were obtained treated plates (a) to (k).

The acrylic copolymer used for obtaining the treated plate (k) was a copolymer of 70 parts of methyl methacrylate and 30 parts of ethyl acrylate.

Table 1

| Treated Plate | Composition of Coating Material (A) | Undercoat Layer Treating Condition |
| --- | --- | --- |
| (a) | mixture of 80 parts of isocyanate compound (II) and 20 parts butyl acrylate | electron beam was irradiated in nitrogen atmosphere so that absorbed dose was 1 Mrad |
| (b) | isocyanate compound (II) | same as above |
| (c) | mixture of 90% of mixture of 80 parts of isocyanate compound (II) and 20 parts of butyl acrylate and 10% of zinc chromate | same as above |
| (d) | isocyanate compound (III) | same as above |
| (e) | mixture of 50 parts of isocyanate compound (IV) and 50 parts of unsaturated resin solution (2) | same as above |
| (f) | isocyanate compound (V) | same as above |
| (g) | mixture of 80 parts of isocyanate compound (VI) and 20 parts of styrene | same as above |
| (h) | mixture of 80 parts of unsaturated resin solution (3) and 20 parts of tolylene diisocyanate | same as above |
| (i) | mixture of 85 parts of coating material used in (h), 10 parts of strontium chromate and 5 parts of triethanolamine | 100°C. hot air was blown for 1 minute |
| (j) | isocyanate compound (I) | allowed to stand still at room temperature for 24 hours |
| (k) | mixture of 20 parts of tolylene diisocyanate, 60 parts of n-butyl acrylate, 10 parts of saturated acrylic (methyl methacrylate-n-butyl methylacrylate) copolymer and 10 parts of zinc chromate | electron beam was irradiated in nitrogen atmosphere so that absorbed dose was 3 Mrad |

Topcoat paints (6) to (10) to be used as coating compositions (B) were prepared by adding 15 parts of titanium oxide and 7 parts of phthalocyanine blue to 100 parts of each of unsaturated resin solutions (1) to (5) to form a mixture and kneading the mixture.

Topcoat paints (6) to (10) were coated on treated plates (a) to (k) and an untreated zinc-plated steel plate in a film thickness of 20 $\mu$, combinations of the topcoat paints with the plates being illustrated in Table 2. Then, each assembly was subjected to the irradiation of electron beam in a nitrogen atmosphere with use of an electron accelerator of an accelerating voltage of 300 Kev, a beam current of 25 mA and a scanning width of 1 m as a source of activating energy rays at a dose rate of 3 Mrad/sec so that the dose absorbed in the coating was 6 Mrad, whereby cured, cross-linked coatings were obtained.

The resulting two-layer composite cross-linked coatings were tested for their properties. The results are shown in Table 2.

The test of the coatings for their properties was made as follows:

Adhesion

Eleven cut-lines were formed at intervals of 1 mm on the coating in either the longitudinal direction or the lateral direction to form 100 cross-cut squares. A cellophane adhesive tape was applied to the coating so cut, and the tape was peeled. The adhesion was expressed in terms of the number of squares left on the base material after peeling of the tape.

Bending Property

The base material having the cross-linked coating thereon was bent at an angle of 180° while keeping outside the coating-formed side of the base material, and a Cellophane adhesive tape was applied to the coating at the bent portion. Then, the tape was peeled, and the condition of the coating was examined.

Impact Resistance

The impact resistance was determined according to Du Pont's falling ball test. Namely, a weight having a point end diameter of one half inch and a load of 1 Kg was let to fall from a height of 50 cm to the coating, and the fracture state of the coating was examined. The state of the coating after the test was evaluated on a scale of (good) >◎>○>△>X (bad).

Corrosion Resistance

The corrosion resistance was determined according to the salt spray test. Namely, a saline solution of a concentration of 5% was sprayed onto the cross-cut coating formed on the base material, and the spraying was continued for 500 hours. The corrosion resistance was expressed in terms of the maximum width of rust formed on the base material (the cross-cut portions).

Table 2

| Topcoat paint | (6) | | | | | | (7) | | | | | | |
|---|---|---|---|---|---|---|---|---|---|---|---|---|---|
| Treated plate | (a) | (b) | (c) | (d) | (e) | untreatd plate | (f) | (g) | (h) | (i) | (j) | (k) | untreated plate |
| Pencil hardness | 2H | 2H | 2H | 2H | 2H | 2H | 3H | 3H | 3H | 3H | 3H | 3H | 3H |
| Adhesion | 100/100 | 100/100 | 100/100 | 95/100 | 100/100 | 0/100 | 100/100 | 100/100 | 100/100 | 100/100 | 100/100 | 100/100 | 5/100 |
| Bending property (1 mm) | not changed | not changed | not changed | slightly peeled | not changed | peeled | not changed | not changed | not changed | not changed | not changed | not changed | peeled |
| Impact resistance | ◎ | ◎ | ◎ | ○ | ◎ | X | ◎ | ○ | ◎ | ◎ | ○ | ◎ | X |
| Corrosion resistance | 1 | 1 | 0~1 | 3 | 1 | 6 | 0~1 | 3 | 1 | 1 | 3 | 0~1 | 10 |

| Topcoat paint | (8) | | | (9) | | | | (10) | | | |
|---|---|---|---|---|---|---|---|---|---|---|---|
| Treated plate | (a) | (b) | untreated plate | (g) | (h) | (i) | untreated plate | (b) | (d) | (f) | untreated plate |
| Pencil hardness | 3H | 3H | 3H | 4H | 4H | 4H | 4H | H~2H | H~2H | H~2H | H~2H |
| Adhesion | 100/100 | 100/100 | 30/100 | 100/100 | 95/100 | 98/100 | 10/100 | 100/100 | 100/100 | 100/100 | 50/100 |
| Bending property (1 mm) | not changed | not changed | peeled | not changed | slightly peeled | slightly peeled | peeled | not changed | not changed | not changed | peeled |
| Impact resistance | ◎ | ◎ | X | ◎ | △ | ○ | X | ◎ | ◎ | ◎ | △ |
| Corrosion resistance | 0 | 0 | 5 | 1~2 | 2~3 | 1~2 | 10 | 2 | 0~1 | 2 | 6 |

As is seen from the results shown in Table 2, the cross-linked coatings obtained according to this invention are excellent in both adhesion to the base material and flexibility.

EXAMPLE 2

Three kinds of coating compositions (A) were prepared by adding 2 parts of benzoin isobutyl ether to 100 parts of each of coating compositions (A) as used in Example 1 for forming treated plates (a), (b) and (c), respectively, and mixing them. These coating compositions were each coated to a film thickness of 5 $\mu$ on a chromic acid-treated aluminum plate as the substrate. The resulting three substrates having a coating formed thereon were exposed to ultraviolet rays emitted from a high pressure mercury lamp of 800 W disposed just above the substrates and 10 cm apart therefrom for 30 seconds to obtain treated plates (a'), (b') and (c'). A coating composition (B) prepared by mixing 100 parts of the unsaturated resin solution (3) and 2 parts of benzoin isobutyl ether was coated on each of the above treated plates (a'), (b') and (c') to a thickness of 30$\mu$, and the irradiation of ultraviolet rays was carried out for 2 minutes under the same conditions as above to effect the cross-linking. The properties of the composite coatings so obtained are shown in Table 3. In Table 3, the results of adhesion and impact resistance are those obtained by conducting the tests in the same manner as in Example 1.

Table 3

| Treated plate | (a') | (b') | (c') | Untreated Plate |
| --- | --- | --- | --- | --- |
| Adherence | 100/100 | 100/100 | 100/100 | 5/100 |
| Erichsen test (mm) | 8 | 5 | 7 | 2 |
| Impact resistance | ◎ | ◎ | ◎ | Δ |
| Boiling water resistance test (2 hours) | not changed | not changed | not changed | peeled |

As is apparent from the results shown in Table 3, the coatings obtained according to this invention exhibit very good adhesion to the base material and excellent corrosion resistance.

EXAMPLE 3

A coating composition (A) was prepared by mixing 100 parts of the isocyanate compound (II) with 20 parts of butyl acrylate and 2 parts of benzoin isopropyl ether, and the composition (A) so prepared was coated to a thickness of 4 $\mu$ on a print hard board. Then, ultraviolet rays having a main wavelength of 3650 A were irradiated onto the coating formed on the board for 30 seconds under the same conditions as in Example 2 to obtain a treated plate (l). A coating composition (B) was prepared by mixing 100 parts of the unsaturated resin solution (6) with 2 parts of benzoin isopropyl ether, and the composition (B) so prepared was coated to a thickness of 50 $\mu$ on each of the treated plate (l) and the aforesaid untreated print hard board, after which ultraviolet rays were irradiated for 2 minutes under the same conditions as in Example 2 to effect the cross-linking reaction in the coating formed on the hard board. The properties of the resulting composite coatings are shown in Table 4. The evaluation of peeling under dipping shown in Table 4 was conducted by dipping the cross-linked coatings formed on the base plates in boiling water for 4 hours, drying them in warm air maintained at 60°C. for 20 hours and observing changes in the condition of the cross-linked coatings.

Table 4

|  | Treated Plate (l) | Untreated Plate |
| --- | --- | --- |
| Pencil hardness | 3H | 3H |
| Adhesion | 100/100 | 25/100 |
| Peeling under dipping | not changed | coating was peeled |

As is apparent from the results shown in Table 4, the coatings obtained according to this invention are excellent in adhesion to the base material and have good resistance against boiling water.

EXAMPLE 4

A mixture of 40 parts of an epoxy compound (Epikote 1001 manufactured by Shell Chemicals), 50 parts of n-butyl acrylate and 10 parts of tetraethylene glycol was incorporated with 5 parts of titanium oxide and 18 parts of strontium chromate as the pigments. Then, 70 parts of the resulting pigment-containing mixture was blended with 30 parts of an isocyanate group-containing adduct formed by reacting xylylene diisocyanate and trimethylol propane in a molar ratio of 3/1 (Takenate D-110N manufactured by Takeda Pharmaceutical Co.), to thereby obtain an undercoat paint (A) which is one form of the coating composition (A). This coating composition (A) was coated to a thickness of 5 $\mu$ on a zinc-plated steel plate treated with zinc phosphate, and electron beam was irradiated onto the resulting coating in the air with use of the same electron accelerator as employed in Example 1, so that the dose absorbed in the coating was 2 Mrad, to thereby obtain a treated plate (m). Then, the topcoat paint (10) which is one form of the resinous coating composition (B), was coated to a thickness of 15 $\mu$ on the treated plate (m), and electron beam was irradiated to the coating in a nitrogen atmosphere so that the absorbed dose was 6 Mrad, to thereby obtain a cured, cross-linked coating. The composite coating so obtained was tested for its properties, and the results are shown in Table 5 given below.

EXAMPLE 5

A treated plate (n) having an undercoat layer was prepared by repeating the coating procedure of Example 4 except that 30 parts of an acrylic thermoplastic resin (acryolid B-82 manufactured by Rhom & Haas CO.) was substituted for 40 parts of the epoxy compound used in Example 4 and conducting the irradiation of electron beam under the same conditions as in Example 4. The topcoat paint (10) was coated on the treated plate (n) in the same manner as in Example 4 and the coating was cured and crosslinked by applying the irradiation of electron beam thereto in the same manner as in Example 4. The resulting composite coating was tested for its properties which are shown in Table 5.

Example 6

A coating composition (A) was prepared in the same manner as in Example 4 except that 30 parts of a vinyl chloride resin (VMCA manufactured by Union Carbide Corporation) was substituted for 40 parts of the epoxy compound used in Example 4, and it was coated to a thickness of 5 μ on a zinc-plated steel plate, following which the irradiation of electron beam was applied to the coating formed on the steel plate in the same manner as in Example 4 to obtain a treated plate (o). The topcoat paint (10) was coated on the treated plate (o) in the same manner as in Example 4 and electron beam was irradiated to the coating under the same conditions as in Example 4, to thereby obtain a composite, cross-linked coating. The properties of the composite coating were determined and the results are shown in Table 5.

EXAMPLE 7

Following the procedure of Example 4, but substituting the coating composition (A) used in Example 4 by a coating composition which was the same as said composition (A) except that the latter did not contain the epoxy compound, a plate with an undercoat layer formed thereon was obtained and the plate so coated was further coated with the topcoat paint (10), followed by being irradiated by electron beam in the same manner as in Example 4 to obtain a cross-linked composite coating (p) the properties of which are shown in Table 5.

Table 5

|  | Treated plate (m) | Treated plate (n) | Treated plate (o) | Treated plate (p) |
| --- | --- | --- | --- | --- |
| Pencil hardness | H – 2H | H – 2H | H – 2H | H – 2H |
| Adhesion | 100/100 | 100/100 | 100/100 | 98/100 |
| Bending property | not changed | not changed | not changed | not changed |
| Impact resistance | ◎ | ◎ | ◎ | ○ |
| Corrosion resistance | 0 – 1 | 0 – 1 | 1 | 1 – 2 |

From the results shown in Table 5, it will readily be understood that cured, cross-linked coatings obtained according to this invention have excellent adhesion and good flexibility.

What is claimed is:

1. A process for the formation of a composite cured coating which comprises:
   1. applying to a base material a coating composition (A) comprising one member selected from the group consisting of (a) an unsaturated isocyanate compound containing both as many ethylenically unsaturated groups as calculated from the formula $$0.5 \text{ to } 12 \times \frac{\text{Molecular Weight of Unsaturated Isocyanate Compound}}{1000}$$

and free isocyanate groups in an amount of 0.5 to 30% by weight of the coating composition (A), (b) a mixture of an unsaturated compound containing as many ethylenically unsaturated groups as calculated from the formula $$0.5 \text{ to } 12 \times \frac{\text{Molecular Weight of Unsaturated Compound}}{1000}$$

and saturated or unsaturated isocyanate compound containing free isocyanate groups in an amount of 0.5 to 30% by weight of the coating composition (A), and (c) a mixture of the material (a) or (b) and a resinous saturated compound, to form an undercoat layer of the composition (A) on the base material,
   2. thereafter applying to the thus-formed undercoat layer a resinous coating composition (B) comprising an unsaturated resin containing as many ethylenically unsaturated groups as calculated from the formula $$0.5 \text{ to } 12 \times \frac{\text{Molecular Weight of Unsaturated Resin}}{1000}$$

to form a topcoat layer on the undercoat layer, and
   3. then subjecting the topcoat and undercoat layers to the irradiation of electron beam or light having a wavelength of 2000 to 8000 A to thereby form the integrated, cured coating on the base material.

2. A process as claimed in claim 1, wherein the undercoat layer is subjected to the irradiation of electron beam or light having a wavelength of 2000 to 8000 A prior to the formation of the topcoat layer thereon.

3. A process as claimed in claim 1, wherein the undercoat and topcoat layers each require a dosage ranging from 1 to 20 Mrad to be cured, the dosage being supplied by the irradiation of the electron beam at a dose rate of from 1 to 20 Mrad/sec or of the light at an output of from 80 to 200 watt/inch for 1 to 30 seconds.

4. A process as claimed in claim 2, wherein the electron beam and the light have each an energy capable of irradiating at a dose rate of from 0.1 to 20 Mrad/sec.

5. A process as claimed in claim 2, wherein the irradiation upon the undercoat layer is effected in an atmosphere containing at least 0.2% of oxygen.

* * * * *